United States Patent [19]

Bauer et al.

[11] 4,016,279

[45] Apr. 5, 1977

[54] SPRAY COMPOSITIONS FOR INHALATION THERAPY OF BRONCHIAL DISORDERS

[75] Inventors: Rudolf Bauer, Wiesbaden; Helmut Wick, Ingelheim, both of Germany

[73] Assignee: Boehringer Ingelheim GmbH, Ingelheim am Rhein, Germany

[22] Filed: Jan. 13, 1976

[21] Appl. No.: 648,729

Related U.S. Application Data

[63] Continuation-in-part of Ser. No. 487,054, July 10, 1974, abandoned, which is a continuation-in-part of Ser. No. 271,558, July 13, 1972, abandoned.

[30] Foreign Application Priority Data

July 13, 1971 Germany .......................... 2134899

[52] U.S. Cl. .................................. 424/265; 424/45; 424/46
[51] Int. Cl.$^2$ ...................... A61L 9/04; A61K 9/14; A61K 31/46
[58] Field of Search ....................... 424/45, 46, 265

[56] References Cited

UNITED STATES PATENTS

| | | | |
|---|---|---|---|
| 2,753,288 | 7/1956 | Visscher | 424/265 |
| 3,169,095 | 2/1965 | Thiel et al. | 424/46 |
| 3,472,861 | 10/1969 | Zeile et al. | 424/253 |

OTHER PUBLICATIONS

Chem. Abst. 51 − 1214i (1967).

*Primary Examiner*—Stanley J. Friedman
*Attorney, Agent, or Firm*—Hammond & Littell

[57] ABSTRACT

Spray compositions, preferably in aerosol form, for inhalation therapy of bronchial disorders, especially acute or chronic asthma and acute or chronic obstructive bronchitis, containing as an active ingredient N-ethyl-norscopolamine methobromide or N-methylscopolammonium bromide optionally in combination with a mucolytic.

4 Claims, No Drawings

SPRAY COMPOSITIONS FOR INHALATION THERAPY OF BRONCHIAL DISORDERS

This is a continuation-in-part of copending application Ser. No. 487,054 filed July 10, 1974 now abandoned; which is a continuation-in-part of application Ser. No. 272,558 filed July 13, 1972, now abandoned.

This invention relates to novel pharmaceutical spray compositions for inhalation therapy of bronchial disorders, especially acute or chronic asthma and acute or chronic obstructive bronchitis, containing as an active ingredient N-ethyl-norscopolamine methobromide or N-methylscopolammonium bromide, optionally in combination with a mucolytic.

BACKGROUND OF THE INVENTION

Bronchial disorders, especially acute and chronic asthma, are presently treated primarily with bronchodilating catecholamine derivatives, such as isoproterenol or metaproterenol, by means of various highly effective pharmaceutical compositions, such as inhalation sprays, intravenous or intramuscular hypodermic solutions, or orally administerable powders or tablets. These catecholamine derivatives, however, most often produce significant side effects which are typical for this class of compounds, such as tachycardia, cardiac arrhythmia and alterations of blood pressure which may give rise to complications.

It is also known to treat bronchial disorders by intravenous administration of a spasmolytic, but this method is also accompanied by undesirable side effects which are characteristic of spasmolytics, especially mydriasis and dryness of the mouth and tachycardia.

OBJECTS OF THE INVENTION

It is an object of the present invention to provide effective pharmaceutical inhalation spray compositions for the treatment of bronchial disorders, such as asthma and chronic bronchitis, which are completely free from undesirable side effects.

It is another object of the instant invention to provide an effective method for inhalation therapy of bronchial disorders, such as asthma, which does not produce the undesirable side effects often connected with the presently employed treatment methods.

Still other objects and advantages of the invention will become apparent as the description thereof proceeds.

THE INVENTION

We have discovered that the above objects are achieved by means of spray compositions, preferably in aerosol form, comprising as an active ingredient N-ethyl-norscopolamine methobromide or N-methyl scopolammonium bromide, optionally in combination with a mucolytic. N-Ethyl-norscopolamine methobromide is particularly preferred as the active ingredient.

The scopolamine derivatives employed in accordance with the present invention are known compounds. Thus, a. N-ethyl-norscopolamine methobromide is disclosed in German Offenlegungsschrift 1,670,048 and U.S. Pat. No. 3,472,861; and b. N-methyl-scopolammonium bromide is disclosed in U.S. Pat. No. 2,753,288.

The inhalation spray compositions pursuant to the present invention are prepared in conventional manner by dissolving or suspending the active ingredient in a suitable liquid substrate, and filling the resulting solution or suspension into a suitable container from which it can be expelled as an atomized spray or an aerosol through a suitable nozzle or valve. The active ingredient concentration in the solution or suspension should be 0.007 to 1.0% by weight, based on the total weight.

The single effective therapeutic dosage range of N-ethyl-norscopolamine methobromide or N-methyl-scopolammonium bromide for inhalation spray therapy is from 5 to 100 $\gamma$. Normally, a dose of 5 to 50 $\gamma$ is sufficient to relieve bronchial spasms due to acute or chronic asthma or chronic bronchitis while somewhat higher dosages up to 100 $\gamma$ are required to relieve bronchial spasms due to acute bronchitis. consequently, the design of the container should be such that each actuation of the means for expelling the solution or suspension therefrom ejects a measured amount of spray or aerosol containing the desired amount of active ingredient.

The container may be a simple squeeze bottle or piston- or bulb-operated atomizer provided with a suitable atomizing nozzle, or preferably an aerosol spray can provided with a metering aerosol valve.

The inhalation spray compositions according to the present invention may also contain an effective amount of a mucolytic, such as N-cyclohexyl-N-methyl-(2-amino-3,5-dibromo-benzyl)-ammonium chloride or N-acetyl-L(+)-cysteine.

The following examples illustrate the present invention and will enable others skilled in the art to understand it more completely. It should be understood, however, that the invention is not limited solely to the particular examples given below. The percentages are percent by weight.

EXAMPLE 1

Aerosol

The aerosol composition is compounded from the following ingredients:

| | |
|---|---|
| N-ethyl-norscopolamine methobromide | 0.007 – 0.7% |
| Sorbitan trioleate (surfactant) | 0.5 – 2% |
| Mixture of monofluoro-trichloromethane and difluoro-dichloromethane (40 : 60) | q.s.ad 100% |

Preparation

The ingredients are admixed with each other in conventional fashion, and the mixture is filled into aerosol spray cans provided with a metering valve which meters out with each actuation an amount of aerosol containing from 5 to 100 $\gamma$ of the norscopolamine compound. The aerosol expelled from the spray can is an inhalation spray composition with effective bronchospasmolytic action.

EXAMPLE 2

Inhalation spray with mucolytic

The spray composition is compounded from the following ingredients:

| | |
|---|---|
| N-methyl scopolammonium bromide | 0.007 – 0.5% |
| Solution of N-cyclohexyl-N-methyl-(2-amino-3,5-dibromo-benzyl)-ammonium chloride in distilled | |

| | |
|---|---|
| water (2 mgm/ml) | q.s.ad 100% |

Preparation

The scopolammonium compound is dispersed in the aqueous solution, and the mixture is filled into squeeze bottles provided with an atomizing valve which expels with each squeeze an amount of mist containing 5 to 100 γ of the scopolammonium compound. The mist expelled from the squeeze bottle is an inhalation spray composition with effective bronchospasmolytic and mucolytic action.

The same results are obtained when the aqueous solution of the mucolytic is replaced by an equal amount of an aqueous solution (0.2 gm/ml) of N-acetyl-L(+)-cysteine or cysteine-N-acetic acid hydrochloride.

EXAMPLE 3

Inhalation spray

The spray composition is compounded from the following ingredients:

| | |
|---|---|
| N-ethyl-norscopolamine methobromide | 0.005 – 0.4% |
| Phosphate buffer solution (pH 5) | q.s.ad 100% |

Preparation

The norscopolamine compound is dissolved in the buffer solution, and the resulting solution is filled into bottles provided with a piston-operated atomizer nozzle which expels with each actation of the piston an amount of mist containing 5 to 100 γ of the norscopolamine compound. The mist is an inhalation spray composition with effective bronchospasmolytic action.

The amounts and nature of the inert liquid carrier ingredient in these illustrative examples may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An inhalation spray composition for treating bronchial disorders, consisting essentially of a pharmaceutically inert liquid carrier and 0.007 to 1% by weight, based on the total weight, of N-ethyl-norscopolamine methobromide or N-methyl-scopolammonium bromide.

2. An inhalation spray composition of claim 1, wherein said pharmaceutically inert liquid carrier is a mixture of a major amount of a physiologically acceptable liquified aerosol propellant gas and a minor amount of a surfactant.

3. An inhalation spray composition of claim 1, additionally comprising an effective amount of a mucolytic agent.

4. The method of relieving bronchial spasms in human patients, which comprises administering to said patients by the respiratory route from 5 to 100 γ of N-ethylnorscopolamine methobromide or N-methyl-scopolammonium bromide.

* * * * *